(12) United States Patent
Zheng et al.

(10) Patent No.: US 10,126,366 B2
(45) Date of Patent: Nov. 13, 2018

(54) APPARATUS FOR IN-SITU NMR SPECTROSCOPY OF METAL-AIR AND METAL-FREE AIR BATTERIES

(71) Applicant: Florida State University Research Foundation, Tallahassee, FL (US)

(72) Inventors: Jian-ping Zheng, Tallahassee, FL (US); Annadanesh Shellikeri, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 385 days.

(21) Appl. No.: 14/925,343

(22) Filed: Oct. 28, 2015

(65) Prior Publication Data
US 2016/0116540 A1 Apr. 28, 2016

Related U.S. Application Data

(60) Provisional application No. 62/069,541, filed on Oct. 28, 2014.

(51) Int. Cl.
*G01V 3/00* (2006.01)
*G01R 31/36* (2006.01)
(Continued)

(52) U.S. Cl.
CPC ......... *G01R 31/3606* (2013.01); *G01N 24/08* (2013.01); *H01M 10/4285* (2013.01); *H01M 12/08* (2013.01); *Y02E 60/128* (2013.01)

(58) Field of Classification Search
CPC .............. G01R 33/341; G01R 33/3621; G01R 33/3628; G01R 33/3415; G01R 33/3852; H01M 12/06; H01M 12/04; H01M 12/08
See application file for complete search history.

(56) References Cited

U.S. PATENT DOCUMENTS 8,310,235 B1 11/2012 Gerald et al.
2006/0089550 A1 4/2006 Kitney et al.
(Continued)

OTHER PUBLICATIONS

International Search Report mailed in PCT/US15157794 dated Jul. 15, 2016.
(Continued)

*Primary Examiner* — Minh N Tang
(74) *Attorney, Agent, or Firm* — Fox Rothschild LLP

(57) ABSTRACT

An apparatus for the in situ NMR monitoring of a battery including an anode, a separator and an air cathode is provided. The apparatus includes a non-metallic anode container portion, a non-metallic cathode container portion, and non-metallic connecting structure and sealing structure for connecting and sealing the anode container portion and the cathode container portion to define a hermetically sealed interior space for containing the battery with an anode of the battery adjacent the anode container portion and an air cathode of the battery adjacent the cathode container portion. The cathode container portion includes an air chamber portion with an air inlet and an air outlet. The air chamber portion can be adjacent to the air cathode such that air flowing from the air inlet to the air outlet will contact the air cathode. A method of evaluating an air cathode battery and a battery assembly for the NMR spectroscopy of an air cathode battery are also disclosed.

18 Claims, 13 Drawing Sheets

(51) Int. Cl.
*H01M 12/08* (2006.01)
*H01M 10/42* (2006.01)
*G01N 24/08* (2006.01)

(56) References Cited

U.S. PATENT DOCUMENTS

2007/0077485 A1* 4/2007 Takamura ............ H01M 2/0255
429/82
2011/0065016 A1   3/2011  Sata et al.
2011/0281190 A1  11/2011  Skinkle
2012/0214074 A1   8/2012  Sato et al.

OTHER PUBLICATIONS

Leskes et al., "Monitoring the Electrochemical Processes in the Lithium-Air Battery by Solid State NMR Spectroscopy." dx.doi.org/10.1021/jp410429k, J. Phys. Chem. C 2013, 117, 26929-26939 Available: Nov. 27, 2013.

* cited by examiner (a)

(b)

Anode Side  Air Cathode Side

APPARATUS FOR IN-SITU NMR SPECTROSCOPY OF METAL-AIR AND METAL-FREE AIR BATTERIES

CROSS-REFERENCE TO RELATED APPLICATION

This application claims priority to U.S. Application No. 62/069,541, filed Oct. 28, 2014, entitled APPARATUS FOR IN-SITU NMR SPECTROSCOPY OF METAL-AIR AND METAL-FREE AIR BATTERIES, the entirety of which is incorporated herein by reference.

STATEMENT REGARDING FEDERALLY SPONSORED RESEARCH

This invention was made with government support under contract No. GTS-S-13-024 awarded by GTS/US Army. The government has certain rights in this invention.

FIELD OF THE INVENTION

This invention relates generally to metal-air and metal-free air batteries, and more particularly to apparatus and methods for monitoring the operation of such batteries.

BACKGROUND OF THE INVENTION

Lithium (Li)-air batteries, with their large theoretical specific energy (<11,000 Wh g$^{-1}$), are one of the most promising energy-storage technologies, attracting much attention and several studies, with potential applications in transportation, portable devices and grid energy storage. This large theoretic specific energy is possible mainly because (i) the Li-oxygen ($O_2$) couple exhibits a large potential (~3.1V) vs Li/Li$^+$ and (ii) Li metal has a high theoretical specific capacity (3862 mAh g$^{-1}$).

The Li-air battery is often comprised of a Li metal anode, an electrolyte soaked separator, and a carbon air-cathode. During the discharge process, $O_2$ dissolves into the electrolyte from the air cathode side which is open to the atmosphere and gets reduced on the carbon surface which is wetted by electrolyte, forming lithium peroxide ($Li_2O_2$) and lithium oxide ($Li_2O$) as discharge products. $Li_2O$ formation is undesirable since it is irreversible during the charge process. This reaction continues until any one of the active components, namely Li metal, dissolved $O_2$ and active carbon sites in the porous carbon network are exhausted. The overall reactions involved during the discharge/charge processes in rechargeable li-air battery using aprotic organic electrolytes is as shown below:

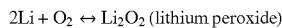

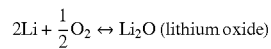

At an early stage in their development, Li-air batteries have to overcome many challenges before they can be applied to practical applications. They are significantly affected by several factors, like the electrolyte salts, cathode pore volume and loading, catalysts, the effect of lithium anode plating/stripping on the solid electrolyte interface (SEI) due to volume changes, $O_2$ partial pressure, and other factors. Clearly, to improve the efficiency and capacity of metal-air and nonmetal-air batteries, deep insight is necessary into the reaction mechanisms of Li-air batteries during discharge and charge processes.

Nuclear magnetic resonance (NMR) is a physical phenomenon exploiting the magnetic properties of certain nuclei and used to study the physical and chemical properties of materials in a process called NMR spectroscopy. It has proven to be an effective analysis technique for Li-ion batteries and supercapacitors; it can provide invaluable information about chemical and structural changes in energy storage devices. Especially, in-situ $^7$Li NMR technique for Li-ion batteries and supercapacitors, has enabled to investigate, in real time, the chemical and structural changes that arise in electrode materials during cycling. Letellier, M.; Chevallier, F.; Beguin, F.; Frackowiak, E.; Rouzaud, J.-N., J. Phys. Chem. Solids 2004, 65, 245-251; and H. Wang, T. K.-J. Köster, N. M. Trease, J. Segalini, P-L. Taberna, P. Simon, Y. Gogotsi and C. P. Grey, J. Am. Chem. Soc., 2011, 133 (48), pp 19270-19273. These previous studies have proven the effectiveness of in-situ NMR technique in helping us understand the functioning of electrochemical energy storage devices, elaborating on the conditions of their failure and identifying new potential materials for use in batteries and supercapacitors.

NMR has been used previously to investigate Li-Air batteries. J. Xiao, J. Hu, D. Wang, D. Hu, W. Xu, G. L. Graff, Z. Nie, J. Liu, J. G. Zhang, J. Power Sources, 196 (2011), 5674-5678; M. Leskes, N. E. Drewett, L. J. Hardwick, P. G. Bruce, G. R. Goward, C. P. Grey, Angew. Chem. Int. Ed. 2012, 51, 8560-8563; L. A. Huff, J. L. Rapp, L. Zhu, A. A. Gewirth, J. Power Sources, 235 (2013), 87-94; and M. Leskes, A. J. Moore, G. R. Goward, and C. P. Grey, J. Phys. Chem. C 2013, 117, 26929-26939. These were ex-situ studies; which were performed pre- and post-cycling after disassembling the cell, which may invite many undesirable complications including the possibility of additional discharging and the effects of evaporation of solvents upon disassembly and the resulting accumulation of salts in the porous carbon network.

SUMMARY OF THE INVENTION

An apparatus for the in situ NMR monitoring of a battery comprising an anode and an air cathode, includes a non-metallic anode container portion and a non-metallic cathode container portion. Non-metallic connecting structure is provided for connecting the anode container portion and the cathode container portion to define an interior space for containing the battery with an anode of the battery adjacent the anode container portion and an air cathode of the battery adjacent the cathode container portion. Non-metallic sealing structure is provided for hermetically sealing the anode portion and the cathode container portion. The cathode container portion includes an air chamber portion with an air inlet and an air outlet. The air chamber portion is adjacent to the air cathode such that air flowing from the air inlet to the air outlet will contact the air cathode.

The sealing structure can include a sealing gasket. The connecting structure can include a non-metallic clamp. The non-metallic clamp can include an annular clamp member defining an opening for receiving the anode container portion and the cathode container portion, and a force-applying member for applying a clamping force to hermetically connect and seal the anode container portion and the cathode container portion. The force-applying member can be a screw.

The apparatus can further include an NMR coil wrapped around the anode container portion and the cathode container portion. The range for inside diameter coil to anode and cathode container dimension ratios can be between 0.3-0.7 in length, 1.02-1.5 in width and 1.01-1.1 in height. The volumetric flow capacity of the air inlet can exceed the volumetric flow capacity of the air outlet to create a positive pressure within the air chamber portion.

The apparatus can be comprised of at least one selected from the group consisting of high density polyethylene (HDPE), acetal homopolymer resin, polychlorotrifluoro ethane polymer (PCTFE), polyetheretherketone (PEEK) plastic, and polyamide-imide (PAI).

The cathode container portion can include walls defining the air chamber portion. The walls can have contact surfaces for contacting the air cathode.

A method of evaluating an air cathode battery, includes the step of securing the battery including the anode and air cathode in a hermetically sealed, non-metallic battery container apparatus. The battery and the container are placed into a nuclear magnetic resonance (NMR) device. Gas comprising oxygen is flowed into and out of the container to contact the air cathode of the battery. The battery is operated. The operation of the air cathode battery is monitored in situ by recording multiple NMR spectra over time as the air cathode battery is operating.

The container can include a non-metallic anode container portion, a non-metallic cathode container portion, and non-metallic connecting structure and sealing structure for hermetically connecting and sealing the anode container portion and the cathode container portion to define a hermetically sealed interior space for containing the battery with an anode of the battery adjacent the anode container portion and an air cathode of the battery adjacent the cathode container portion. The cathode container portion can include a gas chamber portion with a gas inlet and a gas outlet. The gas chamber portion can be adjacent to the air cathode such that gas flowing from the gas inlet to the gas outlet will contact the air cathode.

The method can further include the step of creating a positive gas pressure within the gas chamber portion with the flow of gas by restricting the flow of gas from the gas chamber portion relative to the flow of gas into the gas chamber portion. The step of placing the battery and the container into a NMR device can include the step of inserting the container within an NMR coil.

A battery assembly for the NMR spectroscopy of an air cathode battery includes a battery comprising an anode and an air cathode. A container for the battery includes a non-metallic anode container portion; a non-metallic cathode container portion; non-metallic connecting structure and sealing structure for hermetically connecting and sealing the anode container portion and the cathode container portion to define a hermetically sealed interior space for containing the battery with an anode of the battery adjacent the anode container portion and an air cathode of the battery adjacent the cathode container portion. The cathode container portion includes an air chamber portion with an air inlet and an air outlet. The air chamber portion can be adjacent to the air cathode such that air flowing from the air inlet to the air outlet will contact the air cathode.

The battery can include a separator. The air cathode portion can include titanium. The battery can include a non-ferromagnetic cathode current collector and a non-ferromagnetic anode current collector.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
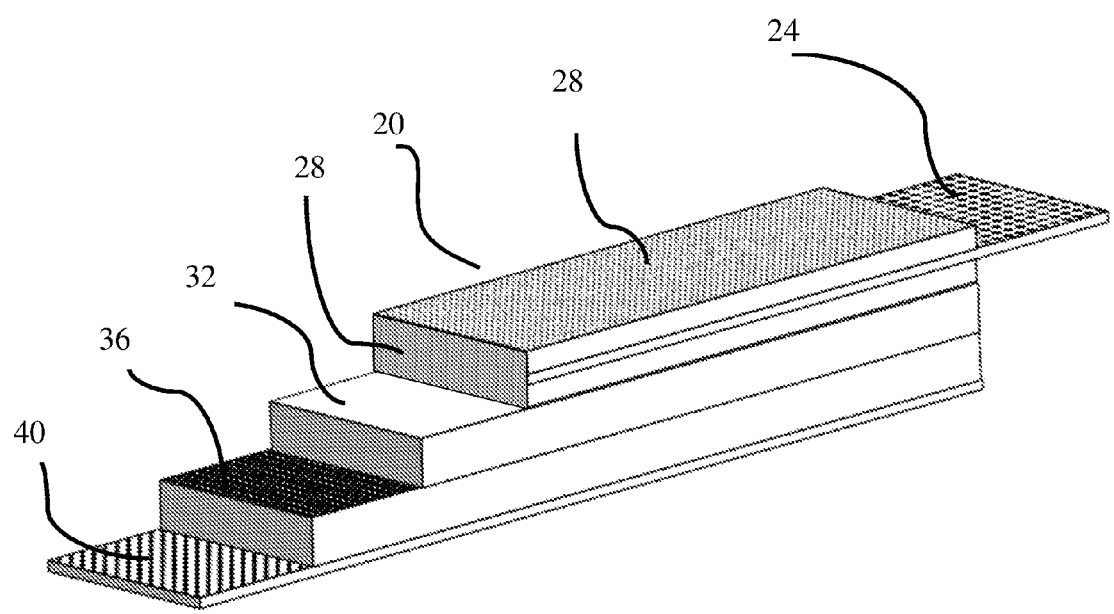
FIG. 1 is a perspective view of a layered Li-Air battery cell structure.

The performance of an in-situ NMR measurement of a battery/capacitor requires that the in-situ cell meets some critical design challenges. Unlike other energy storage devices for example Li-ion batteries and symmetric/asymmetric supercapacitors, which require a straightforward enclosure, Li-air batteries demand complex architecture. The electrolyte soaked porous air-cathode needs to be exposed to a continuous supply of oxygen and yet the anode is to be isolated from this gas flow and moisture to prevent lithium corrosion by maintaining a hermetic seal barrier. These features present technical and design challenges in applying the in-situ NMR technique to Li-air batteries, which is further made complex due to the size limitation introduced by the NMR coil.

An apparatus for the in situ NMR monitoring of a battery including an anode and an air cathode includes a non-metallic anode container portion and a non-metallic cathode container portion. The invention utilizes non-metallic components, or where necessary as for some current collectors, non-ferromagnetic components. Non-metallic connecting structure is provided for connecting the anode portion and the cathode portion to define an interior space for containing the battery with an anode of the battery adjacent the anode container portion and an air cathode of the battery adjacent the cathode container portion. Non-metallic sealing structure is provided for hermetically sealing the anode container portion and the cathode container portion. The connecting structure and the sealing structure can be separate components or integral. The cathode container portion includes an air chamber portion with an air inlet and an air outlet, the air chamber portion being adjacent to the air cathode such that air flowing from the air inlet to the air outlet will contact the air cathode.

The sealing structure can be any suitable structure for hermetically sealing the anode portion to the cathode portion. The hermetic sealing structure can include a sealing non-metallic gasket or O-ring. A groove can be provided to receive the gasket, O-ring, or other sealing component. The sealing structure can include a sealing grease.

The connecting structure can be any suitable non-metallic structure including without limitation clamps, clasps, latches, screws and others. The connecting structure can be formed integrally with the cathode container portion and/or the anode container portion, or can include a separate device. In one aspect the connecting structure include a non-metallic clamp. The non-metallic clamp comprises an annular clamp member defining an opening for receiving the anode container portion and the cathode container portion, and a force-applying member for applying a clamping force to connect the anode container portion and the cathode container portion. The force-applying member can be any suitable structure such as a screw.

The volumetric flow capacity of the air inlet can exceed the volumetric flow capacity of the air outlet to create a positive pressure within the air chamber portion.

The components of the apparatus can be made from any suitable non-metallic material. The material should be somewhat rigid to allow clamping, and chemically inert to the materials being used in the battery. Non-metallic material suitable for the invention include, without limitation, high density polyethylene (HDPE), acetal homopolymer resin, polychlorotrifluoro ethane polymer (PCTFE), polyetheretherketone (PEEK) plastic, and polyamide-imide (PAI).

A method of evaluating an air cathode battery can include the step of securing the battery including the anode and air cathode in a hermetically sealed, non-metallic battery container apparatus. The battery and the container are placed into a nuclear magnetic resonance (NMR) device. Gas comprising oxygen is flowed into and out of the container to contact the air cathode of the battery. The battery is operated, and the operation of the air cathode battery is monitored in situ by recording multiple NMR spectra over time as the air cathode battery is operating.

The container apparatus can comprise a non-metallic anode container portion, a non-metallic cathode container portion, and non-metallic connecting structure and sealing structure for hermetically connecting and sealing the anode container portion and the cathode container portion to define a hermetically sealed interior space for containing the battery with an anode of the battery adjacent the anode container portion and an air cathode of the battery adjacent the cathode container portion. The cathode container portion comprises a gas chamber portion with a gas inlet and a gas outlet, the gas chamber portion being adjacent to the air cathode, such that gas flows from the gas inlet to the gas outlet and contact the air cathode.

The method can include the step of creating a positive gas pressure within the gas chamber portion with the flow of gas by restricting the flow of gas from the gas chamber portion relative to the flow of gas into the gas chamber portion.

A battery assembly for the NMR spectroscopy of an air cathode battery includes a battery comprising an anode and an air cathode, the anode and air cathode being non-ferromagnetic. A container apparatus for the battery includes a non-metallic anode container portion; a non-metallic cathode container portion; connecting structure and sealing for hermetically connecting and sealing the anode container portion and the cathode container portion to define a hermetically sealed interior space for containing the battery with an anode of the battery adjacent the anode container portion and an air cathode of the battery adjacent the cathode container portion. The cathode container portion includes an air chamber portion with an air inlet and an air outlet, the air chamber portion being adjacent to the air cathode such that air flowing from the air inlet to the air outlet will contact the air cathode.

The metal-air battery or nonmetal-air battery can have different designs. The anode of the battery can include different designs and suitable active materials such as an alkali metal like lithium, sodium, or other metals like zinc and tin. Materials such as graphite, grapheme, or a semiconductor like silicon and germanium can be used in a nonmetal-air battery. Other anode materials are also suitable.

The air cathode can be of any suitable design and construction. The air cathode can be an electron conducting porous carbon based material like Vulcan XC 72 carbon, carbon black, acetylene black, carbon fibers, and can include catalyst materials like gold, platinum, and others. A binder can also be present. The air cathode can include a mesh support and current collector for the active material as is known in the art. Titanium can be utilized for such a mesh support, and can be coated with the cathode active material. The cathode air-electrode is made with titanium instead of stainless steel or nickel because of its non-ferromagnetic properties and minimal interference with the bulk magnetic field.

The battery can include current collectors. The current collectors are non-ferromagnetic. Copper and aluminum current collectors, which are diamagnetic and paramagnetic in nature and not ferromagnetic, can be used.

The battery can have a separator. The anode and cathode can be separated by an ionically conductive separator which is in contact with both the anode and cathode. The separator material is chemically compatible with the active metal/materials of the anode/cathode respectively. The separator is an electronically non-conductive material but ionically conductive and may be composed of a polymer such as polyethylene or polypropylene, glass, ceramic, glass-ceramic, sol-gel, among other suitable materials.

An electrolyte can be present. The electrolyte contacts all the components inside the sealed structure and acts as a conductive medium for ion movement. The electrolyte can consist of any suitable material, such as salts like $LiPF_6$, $LiAsF_6$, $LiN(SO_2CF_3)_2$, $LiSO_3CF_3$, $NaPF_6$, $NaAsF_6$, $NaN(SO_2CF_3)_2$, and $NaSO_3CF_3$. The solvents for dissolving these salts can be any of the following: EC, DMC, PC, DEC, THF, EMC, and DME, and also others. These solvents protect the reactive elements of the anode such as lithium and sodium, as well as other parts of the battery like the aprotic electrolytes from reacting with moisture ($H_2O$). A solid electrolyte like $Li_{1.35}T_{1.75}Al_{0.25}P_{2.7}Si_{0.3}O_{12}$ (LTAP), $18.5Li_2O:6.07Al_2O_3:37.05GeO_2:37.05P_2O_5$ (LAGP), can also be used. Other electrolytes are possible.

There is shown in FIG. 1 a perspective layered view of the Li-air battery cell structure. FIG. 1 illustrates the layered structure of a typical metal-air/nonmetal-air battery of the type currently under development where an aprotic (non-aqueous) electrolyte is employed, however, other battery designs and constructions can be utilized. The battery 20 includes a cathode current collector 24, a cathode air electrode 28, and electrolyte soaked separator 32, an anode electrode material 36, and an anode current collector 40.

Figure 2:
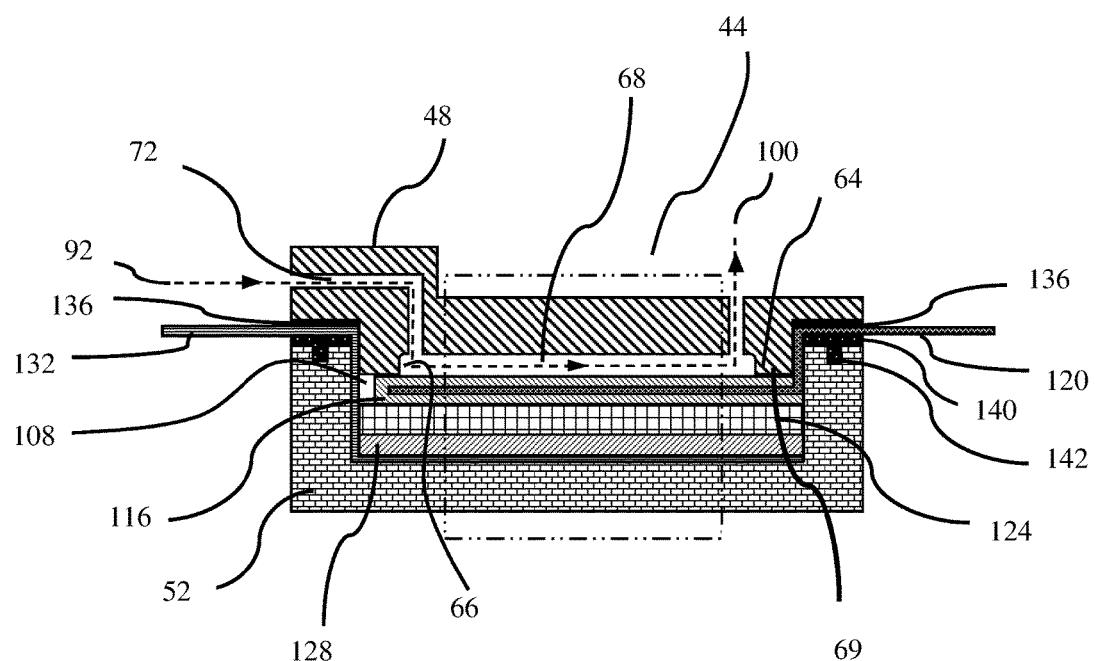
FIG. 2 is a cross sectional view of the Li-air cell apparatus in an assembled state.
Figure 3:
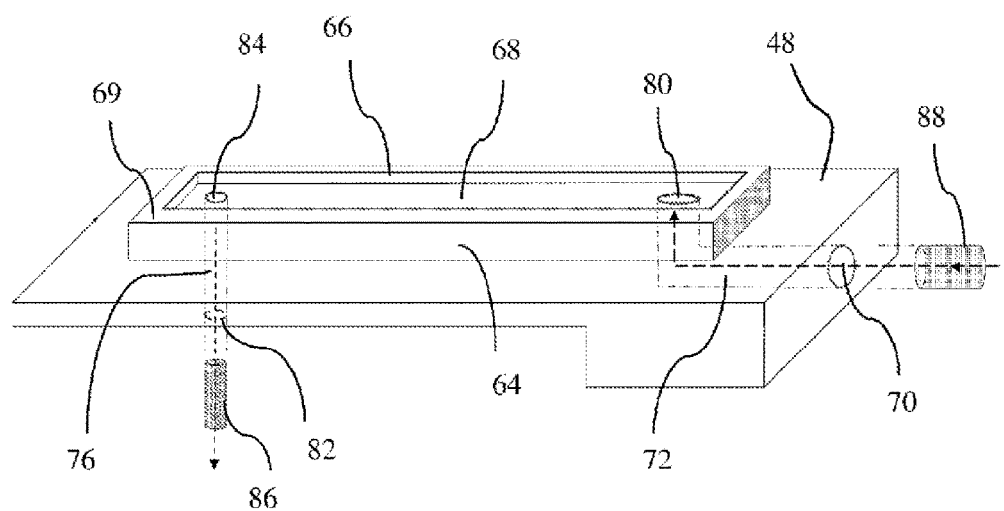
FIG. 3 is a perspective view, partially exploded and partially in phantom, of a cathode portion of the apparatus, inverted to reveal features of the apparatus.
Figure 4:
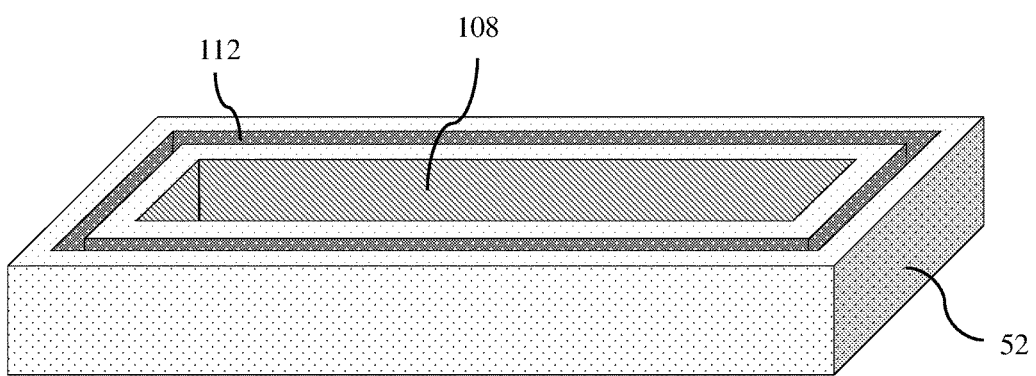
FIG. 4 is a perspective view of an anode portion of the apparatus.

FIGS. 2-4 illustrate a container apparatus 44 and battery assembly according to the invention. The container apparatus 44 includes a cathode container portion 48 and an anode container portion 52. The cathode portion has walls 64 or other suitable structure with interior surfaces 66 to define a gas flow channel or air chamber 68. The walls 64 also define a contact surface 69. A gas inlet channel 72 leads into the air chamber 68 through an inlet opening 80 and an outlet channel 76 permits gas to exit the channel through an outlet opening 82. The anode container portion 52 can include an open interior portion 108 for receiving at least the anode 36 and anode current collector 40 of the battery that is to be analyzed. The open interior portion 108 can be packed with a separator to prevent a direct electrical contact and shorting between the anode and the cathode.

The metal or nonmetal air battery can include an air cathode 116 adjacent the air cathode container portion 48, and an anode 128 adjacent the anode container portion 52. The air cathode communicates with a cathode current collector 120. The anode 128 communicates with an anode current collector 132. A separator 124 can be disposed between the cathode 116 and the anode 120. Suitable sealing structure such as gaskets 136 and 140 can be disposed between the cathode container portion 48 and the anode container portion 52 to form a hermetic seal.

The air chamber 68 directly opens over the air cathode 116 to aerate by oxygen dissolution the electrolyte soaked cathode. The oxygen can be pure $O_2$ for testing purposes, or air or some other gas mixture. Oxygen can flow through an inlet pipe/capillary 88 connected to an inlet aperture 70 which is connected to the air chamber 68 through an inlet channel 72 and inlet opening 80. Oxygen exits from the air chamber 68 through an outlet opening 84 which is connected internally through an outlet channel 76 to an outlet opening external aperture 82 and to an external exhaust pipe/capillary 86 exiting the cell.

The walls 64 defining the air chamber 68 are provided with some width and can be made flat ended and smooth to define the contact surface 69, so that when pressed down on the cathode 116 they make contact with the cathode surface providing an air tight seal for the air chamber 68 to act as an oxygen chamber over the cathode 116 where the oxygen dissolves into electrolyte. The contact surface 69 of the walls 64 provide downward pressure on the sandwich cell structure to reduce contact resistance between the cell layers (FIG. 2). The air chamber 68 is therefore designed such that it performs dual functions. It directly opens over the cathode 116 to aerate the electrolyte soaked cathode 116. The contact portions 69 of the walls 64 defining the air chamber 68 are provided some width and are deliberately made flat ended and smooth while machining so that when pressed down on the cathode 116 by operation of the connecting structure, they will provide sealing pressure on the cathode 116 and reduce contact resistance.

The sealing structure can be provided as gaskets 136 and 140. The gaskets contact and seal the cathode container portion 48 and the anode container portion 52, and can provide a hermetic exit for the cathode current collector 120 and the anode current collector 132. The anode container portion 52 can have a groove 112 for receiving a depending projection 142 of the gasket 140. The groove 112 can also or alternatively receive a sealing putty/high pressure grease or any other sealing agent that is placed inside it after the active cell components (anode, cathode, separator, electrolyte) having been placed in the open interior chamber 108, creating a hermetic seal when the cathode container portion 48 is connected to the anode container portion 52. The groove 112 captures the sealing putty/high pressure grease and forms a hermetic seal between the cathode container portion 48 and the anode container portion 52 while allowing the two electrode current collectors to extend out on two sides of the cell for external connections to a battery cycler.

Figure 5:
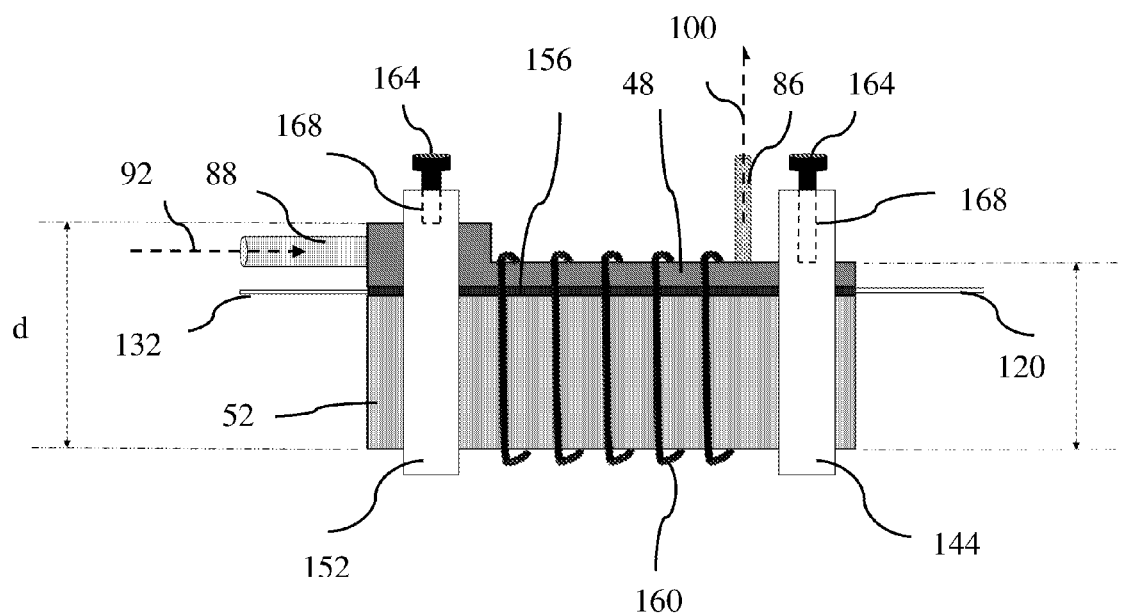
FIG. 5 is a side elevation of a Li-cell apparatus in the assembled state.
Figure 6:
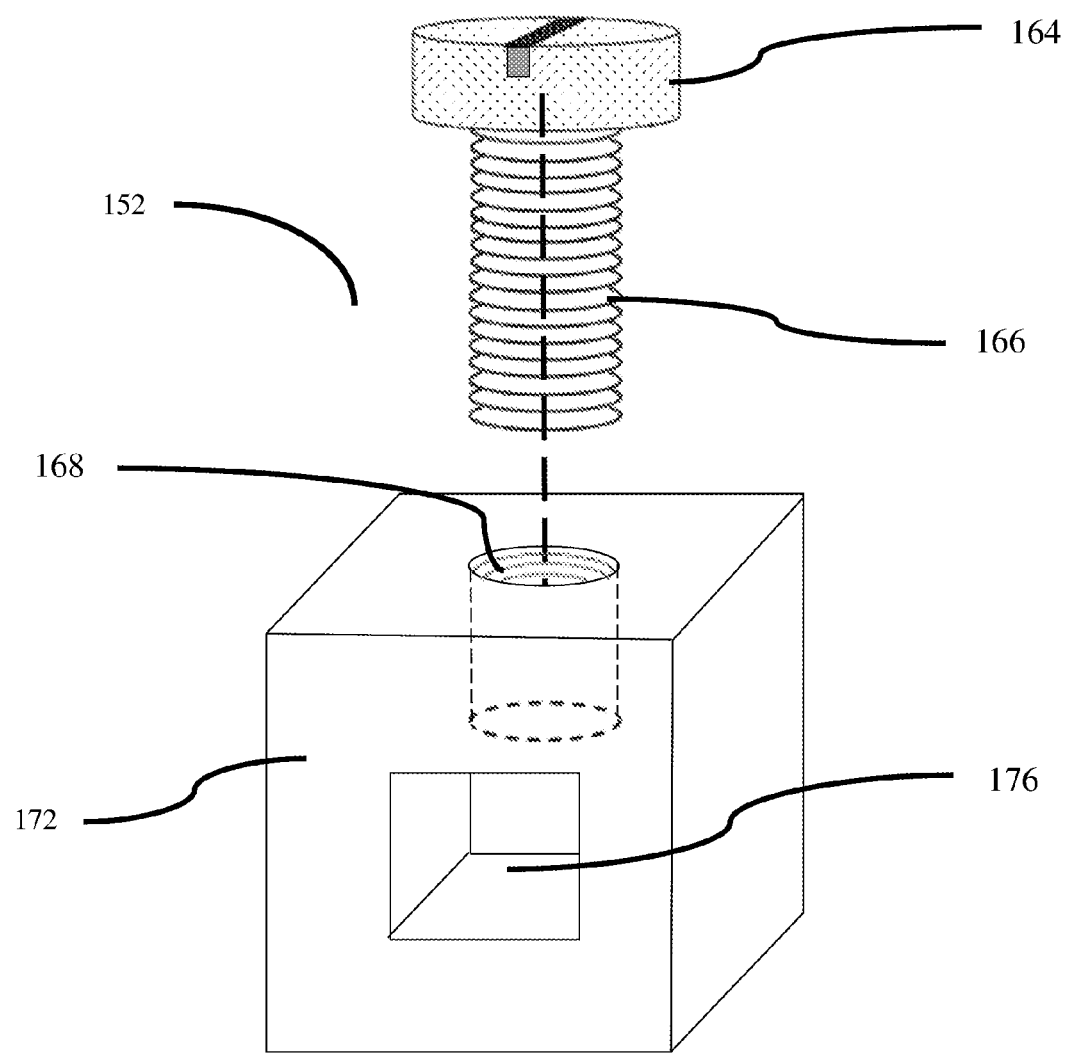
FIG. 6 is a perspective view of a non-metallic clamp.

A pair of non-metallic clamps can be provided on each side of the container apparatus as connecting structure for the cathode container portion 48 and the anode container portion 52. The clamps 144 and 152 (FIG. 5) apply pressure by engaging the cathode container portion 48 and the anode container portion 52. This will apply pressure to the gaskets 136 and 140, to form a hermetic seal between them and possibly also the current collectors 120 and 132. The clamp 152 is depicted in FIG. 6. The clamp 152 can have a clamp body 172 defining an annular opening 176 for receiving the container apparatus 44. A screw 164 with threads 166 can mate with cooperating threads in screw hole 168 to apply pressure to the cell container apparatus 44 and to secure the cathode container portion 48 to the anode container portion 52.

The clamps 144 and 152 can be made of any suitable non-metallic material. The clamps were made from high density polyethylene (HDPE) Delrin material because of its strength and chemical inertness to the aprotic electrolyte used. A screw 164 of same material was used to press down by inserting it through a screw hole 168 in the clamp body 172 with threading created for this purpose.

The container apparatus 44 containing a metal-air/nonmetal-air battery comprising an anode, cathode, ion conductive membrane and electrolyte, is inserted in an NMR coil and then sealed using the clamps 144, 152. The container apparatus 44 dimensions depend on the NMR coil and can vary accordingly with the overall design. The container apparatus 44 can be dimensioned for compatibility with an NMR coil, hence its dimensions can vary according to the dimensions of the NMR coil in use. Custom NMR coils can be fabricated for the container apparatus 44 and battery that will be used.

The container apparatus should fit closely within the NMR coil 160 (FIG. 5) to provide maximum sensitivity of the NMR. The range for inside diameter coil to anode and cathode container dimension ratios being between 0.3-0.7 in length, 1.02-1.5 in width and 1.01-1.1 in height. In an experimental design the NMR coil was designed for a probe for solid state $^7Li$ NMR spectroscopy on 600 MHz (14.1T) magnet and had inside dimensions of $(0.8\times0.4)$ $cm^2$ and a coil length of 1 cm. The container apparatus 44 was designed accordingly with outside dimensions of $(0.75\times0.37)$ $cm^2$ on its smaller side and $(0.75\times0.55)$ $cm^2$ on its larger side (FIG. 5) and 30 cm in length.

The container apparatus 44 and battery can be assembled in glove box with the clamp 152 going on first and tightening the screw 164 through screw hole 168 once the cell is in place, to seal the cathode container portion 48 and anode container portion 52 together with the gaskets 136 and 140 and/or a sealing material like putty or high pressure grease 156 with the anode current collector 132 and cathode current collector 120 extending outside the container apparatus 44. The container apparatus 44 and battery is next inserted into the coil 160 with the smaller side going in first. Once the coil is in place, the cell is hermetically sealed by inserting another clamp 144 on the smaller side and tightening the screw 164 through screw hole 168. This design of the container apparatus 44 enables it to be inserted in the available coil 160 from one side, facilitating the centering of the active cell area in the coil 160 before being hermetically sealed in the glove box inert environment, while being able to circulate oxygen over the cathode, enabling the in-situ NMR tests on metal-air/nonmetal-air batteries.

The air inlet flow path 92 is through an inlet capillary pipe 88 on the larger side of cell while the air outlet flow path 100 is through another outlet capillary pipe 86 towards the smaller side of cell. The effect of diffusion rate of oxygen into the electrolyte on the cell discharge capacity is significant and directly impacts the cell performance, with larger specific capacity observed at higher diffusion rates. The diffusion of oxygen into the electrolyte soaked electrodes is typically accomplished by flowing a stream of oxygen over such electrodes and it is known that higher oxygen partial pressure in the cell yields higher cell capacity in Li-air batteries. The oxygen partial pressure used is higher than the ambient oxygen partial pressure (0.21 atm or 3.086 psi) and can vary in the range 0.21 atm~10 atm (3.086 psi~146.95 psi). A range used to optimize the cell operation was 0.21 atm~4.5 atm (3.086 psi~66.13 psi).

The outlet channel/aperture/pipe/capillary 86 can be made smaller in diameter than that of inlet channel/aperture/pipe/capillary 88 to create positive pressure in the air chamber 68 above the cathode 116 facilitating the dissolution of oxygen into the electrolyte. The inlet to outlet channel/aperture/pipe/capillary diameter ratio may fall in the range of 1:1~1:1.5 dependent on the input oxygen partial pressure used.

The depth of the anode container portion 52 and the open interior portion 108, and the height of the top walls 64, can be reduced or increased by machining the material. Hence this design can be used for testing batteries with different thicknesses of anodes, cathodes and separators.

Figure 7:
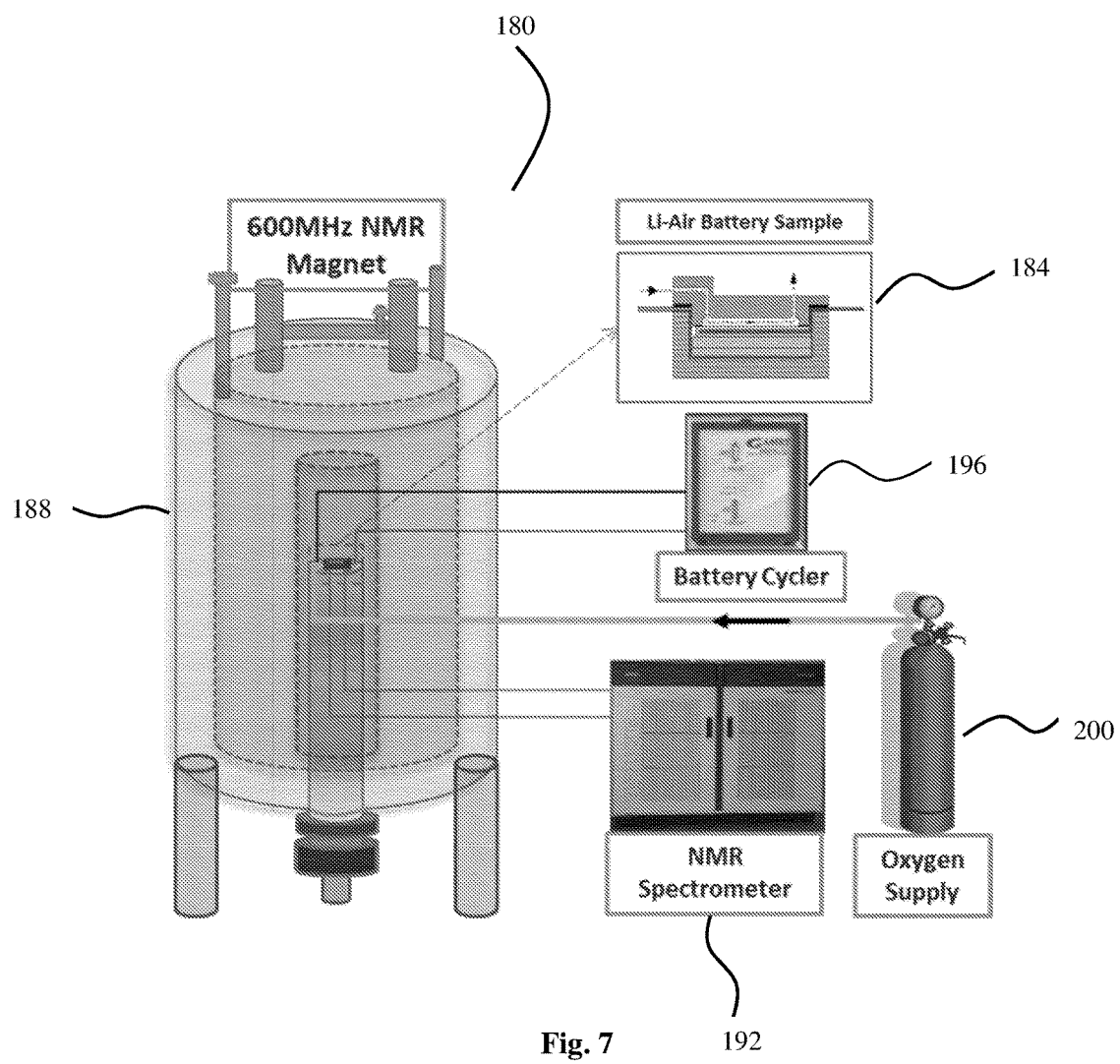
FIG. 7. Is a schematic depiction of an experimental setup for the in-situ $^7$Li NMR spectrometry of Li-air battery

An experimental setup for the in-situ $^7$Li NMR spectrometry of Li-air battery is shown in FIG. 7. The system 180 includes the container apparatus and battery assembly 184 that is positioned in an NMR spectrometer coil 192 of NMR spectrometer 188. A battery cycler 196 is used to operate the battery. An oxygen supply 200 supplies oxygen to the window of the container apparatus during operation of the metal-air/nonmetal-air cell.

Figure 8:
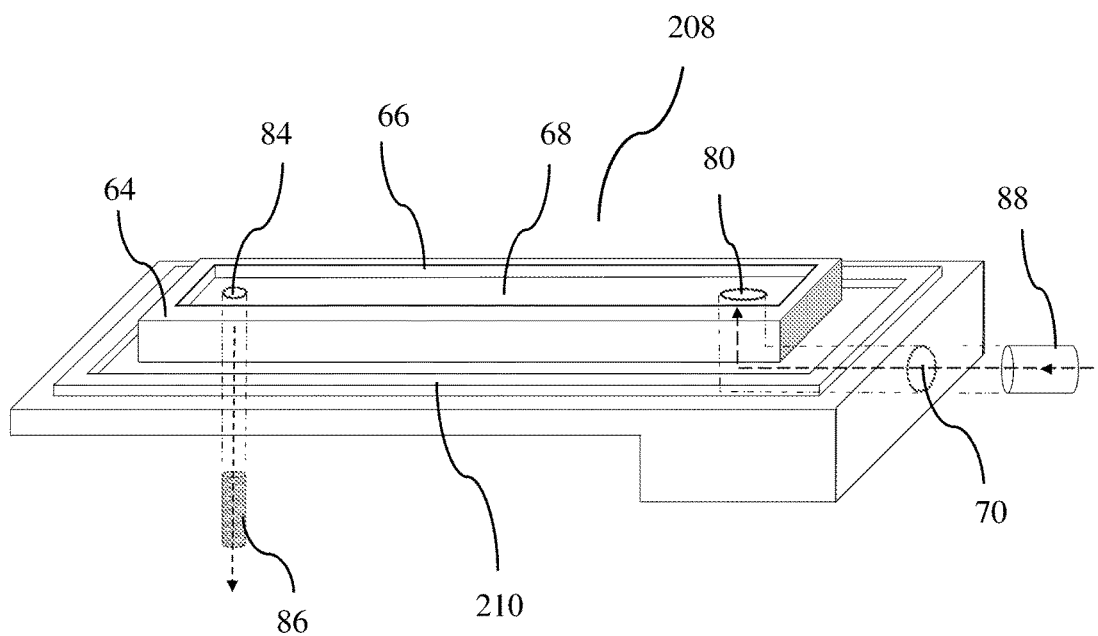
FIG. 8 is a perspective view of an alternative embodiment of a cathode portion inverted to reveal features of the apparatus.

Modifications to the container apparatus 44 are possible. An alternative embodiment of the cathode container portion 208 is shown in FIG. 8. The cathode container portion 208 includes a raised boundary feature 210 around the walls 64. The width and depth of the boundary feature 210 can be selected to mate with the groove 112 (FIG. 4). In one aspect this ratio is 0.5:1 respectively. This further enhances the quality and durability of the hermetic seal formed between the cathode container portion 48 and the anode container portion 52.

Another possible modification is to close the outlet opening 82 and inlet aperture 70 with plugs such as putty/high pressure grease, which will make the container apparatus applicable for testing conventional Li-ion batteries/capacitors.

Mechanically stable standard air electrodes were prepared by first mixing XC72 carbon and carbon black in 1:1 ratio and then forming a paste by mixing with 60 wt % PTFE (DuPont) solution in 85:15 ratio. The mixture was then rolled into thick sheets (500~700 µm) using a hand run roller (Durston rolling mill) and dried in an oven for 2 hrs at 80° C. The dried thick electrode sheets were further rolled to thin out to 150~200 µm. To form the final air electrodes, a titanium mesh was used as current collector which was sandwiched between two thick electrode sheets prepared earlier and exposing the current collector on one end which will later be used for external connection. This was roll pressed using a hand-controlled roller till an electrode thickness of ~200 µm was reached. Electrodes of desired size were cut from this sheet and dried in a vacuum oven overnight at 120° C.

The anode electrode was a Li-metal foil (Sigma Aldrich, 99.9%, 0.75 mm) pressed on to a copper mesh using a die and a hand roller inside the glove box. A non-aqueous electrolyte was prepared with 1 M LiCF$_3$SO$_3$ (Sigma Aldrich, 99.99%) in tetraethylene glycol dimethyl ether (TEGDME) (Sigma Aldrich, 99%).

The Li-air cell was assembled using the cell container apparatus inside an argon atmosphere glove box by stacking a Li foil electrode, a piece of glass fiber separator (20 mm×3.9 mm×0.65 mm) soaked with electrolyte and the prepared air electrode in sequence into the anode container portion, with the air electrode being the topmost. The electrode size used was 18 mm×3.9 mm, for both anode and cathode. A sealing putty/high pressure grease was placed inside the groove designed all around the edge of the anode container portion and the mesh current collector ends were pressed into it, placing the electrodes appropriately in sandwich structure. Then the cell was closed by placing and pressing the cathode container portion into it. The assembled cell measured 30 mm×7.5 mm×3.7 mm in outer dimensions. In this configuration, the diffusion type air electrode which breathes through the titanium mesh current collector, is exposed to the in-coming air only inside air chamber which is directly above it. The air chamber inside the cell was accessible through an inlet line designed in the body of the cathode container portion, which was connected to an external gas line from a cylinder. The outlet line provided inside the cathode container portion directed the gas to outside the cell. A pair of non-metallic clamps was used on each side of the container apparatus to apply pressure to form a hermetic seal. The cell container apparatus was cleaned of any excess putty pushed out by the pressing action, before performing any NMR experiments.

The assembled cell showed an open circuit voltage (OCV) of 3.3V and it was first flushed with oxygen (O$_2$) by flowing O$_2$ for one hour before cycling was started. The flushing helps in removing any argon gas trapped inside the cell container apparatus, since the cell container apparatus and cell are assembled in the inert argon atmosphere of a glovebox. NMR measurements were conducted once cycling started. The test was performed under O$_2$ environment using an inlet supply line connected to the cell container apparatus from an external O$_2$ source. The inlet line was passed through the body of the NMR probe. The Li-air sample cell was inserted in the NMR probe coil, as shown in FIG. 7. The NMR measurements were made using a 600 MHz (14.1 Tesla) high resolution wide bore NMR magnet facility, and a Gamry Potentiostat/Galvanostat (Reference 3000) instrument controlled by a computer was used for cycling purposes.

Figure 9A:
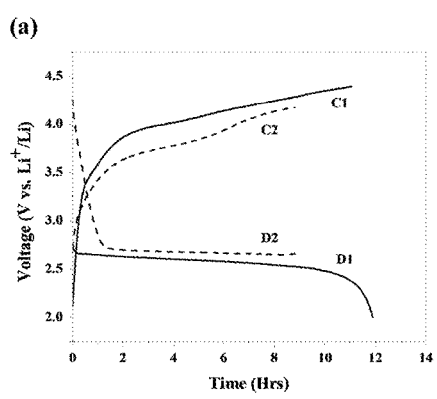
FIG. 9A discharge-charge voltage curves ($1^{st}$ & $2^{nd}$ cycles; and intensity profiles of the cell from the $^7$Li NMR 2D experiments recorded over 42 hrs of cycling ($1^{st}$ and $2^{nd}$ cycles) for the anode side (FIG. 9B) and the air cathode side (FIG. 9C).
Figures 9B, 9C:
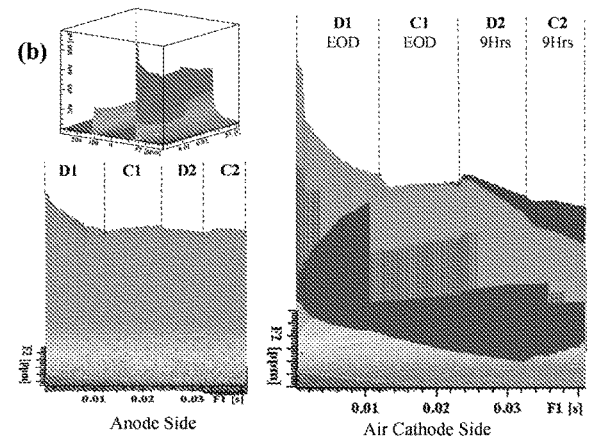
FIG. 9 depicts plots of the results of in-situ experiments on the assembled Li-air cell.

The galvanostatic discharge and charge profiles of $1^{st}$ and $2^{nd}$ cycles of Li—O$_2$ cell assembled using 1 M LiCF$_3$SO$_3$ in TEGDME as electrolyte, are presented in FIG. 9. The discharge part of cycle 1 is designated as D1 and the charge part as C1, and similarly for subsequent cycles. The $1^{st}$ cycle was performed till end of discharge/charge with potential limits of 2V and 4.4V respectively at a current density of 0.1 mA cm$^{-2}$. The second cycle was performed at a current density of 0.05 mA cm$^{-2}$ for a fixed length of time of 9 hrs each. The intensity profiles of the anode and cathode side from the $^7$Li NMR 2D experiments recorded over 42 hrs of cycling (1$^{st}$ and 2$^{nd}$ cycles) are seen in FIG. 9B.

Figure 10:
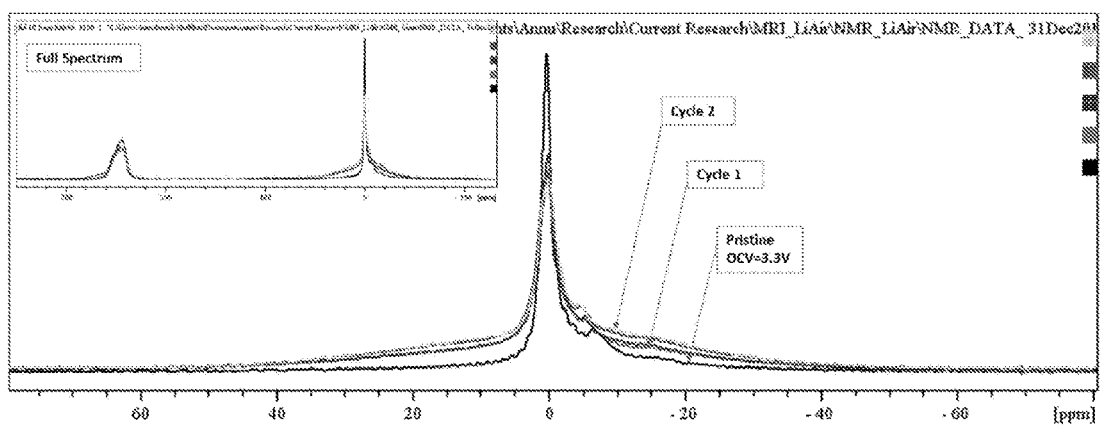
FIG. 10 is in-situ $^7$Li NMR spectra of Li-Air Battery at 14.1 Tesla, for the 1st and 2nd discharge/charge cycles.

The intensity changes can be noted from the discharge/charge profiles, pointing towards a possible consumption of Li-ions from electrolyte, which were introduced by the reduction of lithium metal on contact with the electrolyte, while the broadening of the 0 ppm peak is observed in FIG. 10. The intensity profiles in FIG. 9B also indicate a relatively stable Li-ion concentration in the electrolyte during charge process. This phenomenon was recorded for Li-air batteries in real time using the in-situ NMR spectroscopy of the invention.

The in-situ $^7$Li NMR spectra of Li-air Battery at 14.1 Tesla, for the 1$^{st}$ and 2$^{nd}$ Discharge/Charge Cycles is shown in FIG. 10. FIG. 10 shows the in-situ recorded $^7$Li NMR spectra at 233 MHz (external magnetic field $B_0$=14T) of a single sample of Li-air battery over first two discharge/charge cycles. The NMR spectra of a single sample of Li-air battery over multiple cycles was recorded. In the pristine state of the electrochemical cell (Li-air battery), Li ions in the electrolyte appear in the 0 ppm region as a sharp peak. The anode contributes to the peak centered~250 ppm, relative to the electrolyte species (inset). This shift, known as Knight shift, is a characteristic of the $^7$Li nuclei in a metal and is due to the 'free electron gas' in the metal.

A gradual increase in the area and broadening of the narrow electrolyte peak is observed with the increase in cycling (1st and 2nd discharge), pointing towards the gradual accumulation of discharge products in the porous carbon cathode, with the broadened signal indicating the chemical shift anisotropy pattern of lithium products. This is actually a superposition of a few extremely broad peaks arising from the products formed during the discharging process due to oxidation reactions involving lithium ions.

The origin of broad peaks of products such as $Li_2O_2$ is due to very different magnetic environments presented to the $^7$Li nucleus relative to that of $^7$Li in the electrolyte phase. In the liquid electrolyte phase, the $^7$Li nucleus is subject to rapid and isotropic tumbling and all the broadening inducing magnetic interactions such as quadrupolar, dipolar interactions are averaged to zero, resulting in a single sharp peak. On the other hand, in the case of Li products such as $Li_2O_2$, LiOH (Li hydroxide) or $Li_2CO_3$ (Li carbonate), the product is in solid phase and the electronic environment around the nucleus is predominantly anisotropic. This anisotropy is not averaged to zero. In addition the magnetic dipolar interaction between $^7$Li's spin and various spins and other magnetic moments are not suppressed either. Due to this, these products yield broad NMR lines.

Figure 11A:
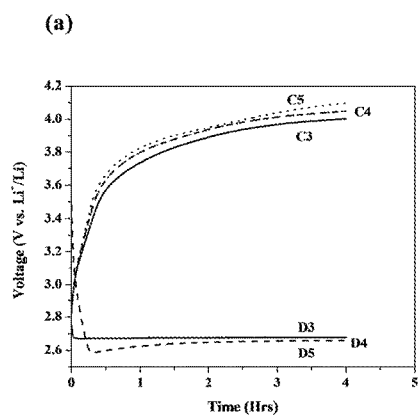
FIG. 11A discharge-charge cycles (3rd, 4th, and 5th) of the assembled Li-Air cell performed for a fixed time of 4 hrs each (0.1 mA/cm$^2$) during in-situ NMR experiments; and intensity profiles of cell from the $^7$Li NMR 2D experiments recorded over 24 hrs of cycling (3rd, 4th, and 5th cycles) for the anode side (FIG. 11B) and the air cathode side (FIG. 11C).

The next three galvanostatic discharge-charge cycles (3$^{rd}$, 4$^{th}$, and 5$^{th}$) were performed one the same Li-air cell sample for a fixed time of 4 hrs each, and the voltage curves recorded are presented in FIG. 11A. A current density of 0.1 mA/cm$^2$ was used for cycling. The discharge part of cycle 3 is designated as D3 and the charge part as C3, and similarly for subsequent cycles. The intensity $^7$Li 2D NMR experiments were performed simultaneously over a total of 24 hrs of galvanostatic cycling of the cell and the intensity profiles are presented in FIG. 9B.

Figure 11B:
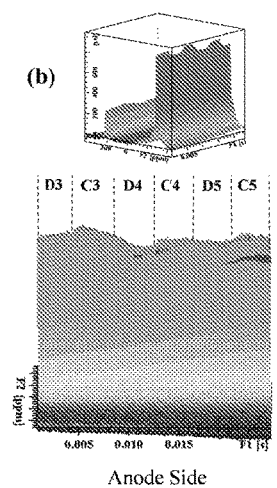
FIG. 11 depicts the results of in-situ experiments on the assembled Li-air cell.
Figure 11C:
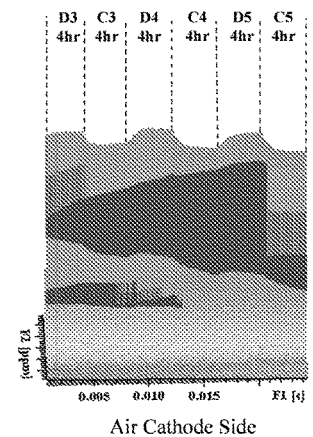

FIG. 11 presents the in-situ experiments on the assembled Li-air cell: (a) Discharge-Charge cycles (3$^{rd}$, 4$^{th}$, and 5$^{th}$) of the assembled Li-Air cell performed for a fixed time of 4 hrs each (0.1 mA/cm$^2$) during in-situ NMR experiments, (b) Intensity profiles of cell from the $^7$Li NMR 2D experiments recorded over 24 hrs of cycling (3$^{rd}$, 4$^{th}$, and 5$^{th}$ cycles).

The pseudo-2d spectrum, shown in FIG. 9B and FIG. 11B allows monitoring of this feature in an in-situ fashion, and we see that in each discharge cycle (D1, D2 in FIG. 9B and D3, D4, D5 in FIG. 11B) the broad peak in the non-metallic (electrolyte) region increases in breadth and intensity.

The pseudo-2d spectra during the 1st two cycles reveals that on the metal side (peak centered~250 ppm, the Knight shift), except for discharge part of the 1st cycle (D1), the intensity remains practically constant. This is consistent w/the skin-depth phenomenon and smooth stripping and deposition on the metal (cathode) side. The discrepancy is only during the D1 which is as yet unexplained.

Figure 12:
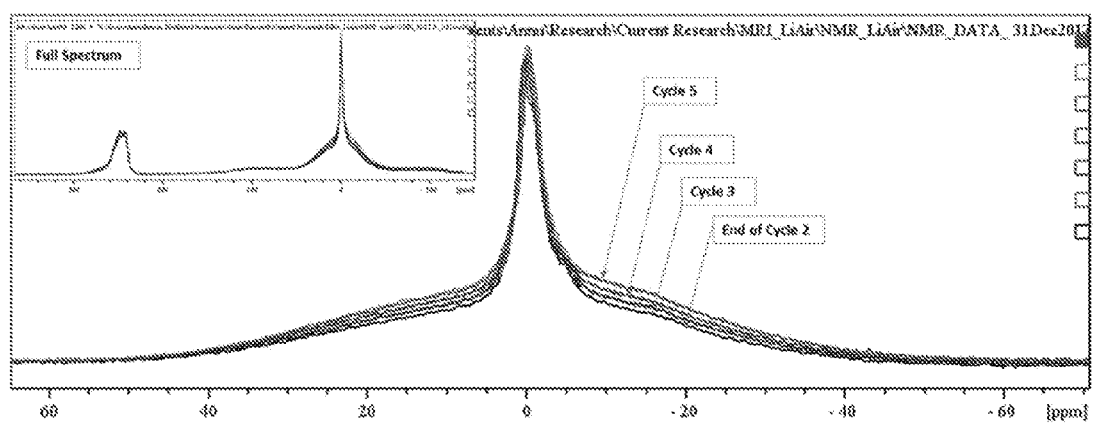
FIG. 12 depicts the in-situ NMR spectra of Li-air battery at 14.1 Tesla, for the 3rd, 4th and 5th discharge/charge cycles.

FIG. 12 presents in-situ NMR spectra of Li-air battery at 14.1 Tesla, for the 3$^{rd}$, 4$^{th}$ and 5$^{th}$ discharge/charge cycles. However, during the charging process, with voltage curves C1 and C2 (FIG. 9A), C3 C4 and C5 (FIG. 11A), if the Li discharge products were completely decomposed back into reactants, the broad peaks should have mostly reduced by the end of charge cycles. However, the pseudo-2d spectra (FIG. 9B and FIG. 11B) are mostly unchanged during this period, as also clearly seen from the spectra of end-of-discharge and end-of-charge states shown in FIG. 10 (cycles 1 and 2). Similar behavior is observed for the remaining cycles, shown in FIG. 12 (cycles 3, 4 and 5).

Figure 13A:
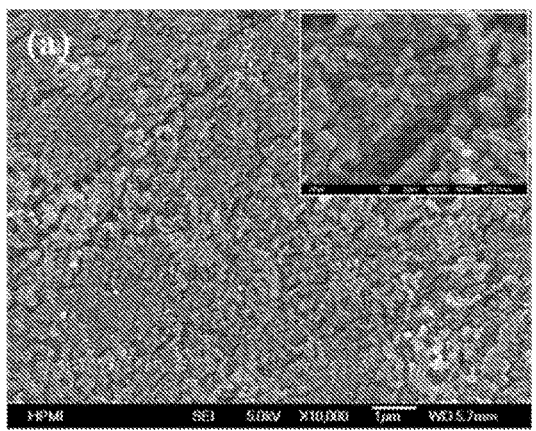
FIG. 13 depicts SEM micrographs of PTFE/XC72/carbon black air-cathodes in the FIG. 13A pristine (undischarged) state.
FIG. 13B discharged state.
Figure 13B:
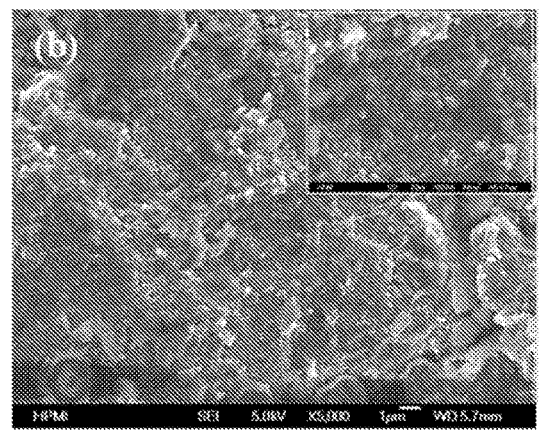

The air-cathode was further characterized using scanning electron microscopy (SEM) using a JEOL SEM (JSM 7401F) instrument to study the morphology and location of the discharge products. The results are presented in FIG. 13. FIG. 13 includes SEM micrographs of PTFE/XC72/carbon black air-cathodes in (a) pristine (undischarged) state, and (b) discharged state SEM micrographs of PTFE/XC72/carbon black air-cathodes (a) Pristine (undischarged) state (b) discharged state are shown in FIG. 13. The SEM images were taken from the surface of air cathodes on the $O_2$ side. The carbon cathode in its pristine state (before discharge) is observed to have a relatively uniform porous structure free of any deposit, as expected and shows the porous nature of the electrode, as seen in FIG. 13A. After 5 discharge/charge cycles, the cell was disassembled and the carbon cathode was washed with acetonitrile solution to remove the electrolyte salt before its air side was investigated for discharge products using SEM. As seen in FIG. 13B, much discharge products are seen deposited in the porous carbon structure, almost filling it, which marks the end of discharge.

To confirm the integrity of the seals, the cell was disassembled inside the glovebox in argon atmosphere at the end of experiments and the Li anode was investigated for corrosion from moisture penetration through seals. The metal electrode was found to be intact and devoid of any white powdery oxide formation, confirming the durability of the seal and the effectiveness of the cell design in blocking the moisture and keeping it external to the cell.

This in-situ cell was designed specifically for Li-air batteries but with minor modifications in depth of enclosures, can be adapted, in general, for in-situ NMR investigation of other metal-air batteries, which have grown in importance like zinc-air, iron-air, aluminum-air and metal-free air batteries involving graphite and silicon anodes. Apparatus described in this invention disclosure can be used not only for in-situ NMR spectroscopy of metal-air and metal-free air batteries, but also for other electrochemical systems such as Li-ion batteries, Li-ion capacitors, super-capacitors.

One of the major challenges to electrification of transportation i.e. a 'true' electric vehicle (EV) is the 'range problem'. Presently, Li-ion batteries can provide a range of about 100 miles (avg.), which greatly restricts the commercial adoption of EVs, especially when the gasoline run vehicles can provide a much larger ranges. Li-air battery research has gained prime importance due to its large theoretical specific energy (<11,000 Wh g$^{-1}$), which rivals traditional gasoline-powered engines, making them one of the most promising energy-storage technologies for EV's. Many challenges have to be met before Li-air batteries can be adopted for EVs and much research is towards solving these problems. In-situ NMR on Li-air batteries can provide vital information about chemical and structural changes, which is critical in mitigating the challenges facing this energy storage device. It is in this regard that the present invention on Li-air battery design for in-situ nuclear magnetic resonance spectroscopy is significant and if this design is commercialized will be primarily be used in industrial R&D, premiere research institutes and national laboratories, in advancing the electric vehicle research through battery developmental work.

This invention can be embodied in other forms without departing from the spirit or essential attributes thereof, and accordingly reference should be had to the foregoing specification and the following claims to determine the scope of the invention.

We claim:

1. An apparatus for the in situ NMR monitoring of a battery comprising an anode and an air cathode during cycling of the cell, the apparatus comprising:
a non-metallic anode container portion;
a non-metallic cathode container portion;
non-metallic connecting structure for connecting the anode container portion and the cathode container portion to define an interior space for containing the battery with an anode of the battery adjacent the anode container portion and an air cathode of the battery adjacent the cathode container portion;
non-metallic sealing structure for hermetically sealing the anode container portion and the cathode container portion, the sealing structure comprising a first sealing portion in the cathode container portion; and,
the cathode container portion comprising an air chamber portion with an air inlet and an air outlet, the air chamber portion being adjacent to the air cathode such that air flowing from the air inlet to the air outlet will contact the air cathode, the cathode container portion comprising a second sealing portion for sealing the air chamber portion to the air cathode, the first and second sealing portions each forming seals when the cathode container portion is joined to the anode container portion.

2. The apparatus of claim 1, wherein the sealing structure comprises a sealing gasket.

3. The apparatus of claim 1, wherein the connecting structure comprises a non-metallic clamp.

4. The apparatus of claim 1, wherein the volumetric flow capacity of the air inlet exceeds the volumetric flow capacity of the air outlet to create a positive pressure within the air chamber portion.

5. The apparatus of claim 1, wherein the apparatus comprises at least one selected from the group consisting of high density polyethylene (HDPE), acetal homopolymer resin, polychlorotrifluoro ethane polymer (PCTFE), polyetheretherketone (PEEK) plastic, and polyamide-imide (PAI).

6. The apparatus of claim 1, wherein the cathode container portion comprises walls defining the air chamber portion.

7. The apparatus of claim 6, wherein the second sealing portion comprises contact surfaces provided on the walls for contacting the air cathode.

8. An apparatus for the in situ NMR monitoring of a battery comprising an anode and an air cathode, the apparatus comprising:
a non-metallic anode container portion;
a non-metallic cathode container portion;
connecting structure for connecting the anode container portion and the cathode container portion to define an interior space for containing the battery with an anode of the battery adjacent the anode container portion and an air cathode of the battery adjacent the cathode container portion, wherein the connecting structure comprises a non-metallic clamp, wherein the non-metallic clamp comprises an annular clamp member defining an opening for receiving the anode container portion and the cathode container portion, and a force-applying member for applying a clamping force to hermetically seal the anode container portion and the cathode container portion;
sealing structure for hermetically sealing the anode container portion and the cathode container portion; and,
the cathode container portion comprising an air chamber portion with an air inlet and an air outlet, the air chamber portion being adjacent to the air cathode such that air flowing from the air inlet to the air outlet will contact the air cathode.

9. The apparatus of claim 8, wherein the force-applying member comprises a screw.

10. An apparatus for the in situ NMR monitoring of a battery comprising an anode and an air cathode, the apparatus comprising:
a non-metallic anode container portion;
a non-metallic cathode container portion;
connecting structure for connecting the anode container portion and the cathode container portion to define an interior space for containing the battery with an anode of the battery adjacent the anode container portion and an air cathode of the battery adjacent the cathode container portion;
sealing structure for hermetically sealing the anode container portion and the cathode container portion; and,
the cathode container portion comprising an air chamber portion with an air inlet and an air outlet, the air chamber portion being adjacent to the air cathode such that air flowing from the air inlet to the air outlet will contact the air cathode; and,
the apparatus further comprising an NMR coil wrapped around the anode container portion and the cathode container portion, the range for inside diameter coil to anode and cathode container dimension ratios being between 0.3-0.7 in length, 1.02-1.5 in width and 1.01-1.1 in height.

11. A method of evaluating an air cathode battery in situ during cycling of the cell, comprising the steps of:
securing the battery including the anode and air cathode in a hermetically sealed, non-metallic battery container apparatus, wherein the container apparatus comprises a non-metallic anode container portion, a non-metallic cathode container portion, and non-metallic connecting structure and sealing structure for hermetically connecting and sealing the anode container portion and the cathode container portion to define a hermetically sealed interior space for containing the battery with an anode of the battery adjacent the anode container portion and an air cathode of the battery adjacent the cathode container portion, the sealing structure comprising a first sealing portion in the cathode container portion; and wherein the cathode container portion comprises an air chamber portion with an air inlet and an air outlet, the air chamber portion being adjacent to the air cathode such that air flowing from the air inlet to the air outlet will contact the air cathode, the cathode container portion comprising a second sealing portion for sealing the air chamber portion to the air cathode, the securing comprising joining the cathode container portion to the anode container portion, the first and second sealing portions each forming seals when the cathode container portion is joined to the anode container portion;

placing the battery and the container into a nuclear magnetic resonance (NMR) device;

flowing air gas comprising oxygen into and out of the container to contact the air cathode of the battery;

operating the battery;

monitoring the operation of the air cathode battery in situ by recording multiple NMR spectra over time as the air cathode battery is operating.

12. The method of claim 11, further comprising the step of creating a positive gas pressure within the gas chamber portion with the flow of gas by restricting the flow of gas from the gas chamber portion relative to the flow of gas into the gas chamber portion.

13. The method of claim 11, wherein the step of placing the battery and the container into a NMR device comprises the step of inserting the container within an NMR coil.

14. The method of claim 11, wherein the apparatus comprises at least one selected from the group consisting of high density polyethylene (HDPE), acetal homopolymer resin, polychlorotrifluoro ethane polymer (PCTFE), polyetheretherketone (PEEK) plastic, and polyamide-imide (PAI).

15. A battery assembly for the in situ NMR spectroscopy of an air cathode battery comprising:

a battery comprising an anode and an air cathode;

a container for the battery comprising a non-metallic anode container portion;

a non-metallic cathode container portion; non-metallic connecting structure and sealing structure for hermetically connecting and sealing the anode container portion and the cathode container portion to define a hermetically sealed interior space for containing the battery with an anode of the battery adjacent the anode container portion and an air cathode of the battery adjacent the cathode container portion, the sealing structure comprising a first sealing portion in the cathode container portion; and the cathode container portion comprising an air chamber portion with an air inlet and an air outlet, the air chamber portion being adjacent to the air cathode such that air flowing from the air inlet to the air outlet will contact the air cathode, the cathode container portion comprising a second sealing portion for sealing the air chamber portion to the air cathode, the first and second sealing portions each forming seals when the cathode container portion is joined to the anode container portion.

16. The battery assembly of claim 15, wherein the battery comprises a separator.

17. The battery assembly of claim 15, wherein the air cathode portion comprises titanium.

18. The battery assembly of claim 15, wherein the battery comprises a non-ferromagnetic cathode current collector and a non-ferromagnetic anode current collector.

* * * * *